United States Patent
Weissman

(10) Patent No.: US 10,548,377 B1
(45) Date of Patent: Feb. 4, 2020

(54) METHODS, SYSTEMS, AND MEDIA FOR RATING AND ANALYZING DIAMONDS

(71) Applicant: The Diamond Pro, LTD, Sarnen (CH)

(72) Inventor: Ira Brookoff Weissman, Maaleh Adumim (IL)

(73) Assignee: The Diamond Pro, LTD (CH)

( * ) Notice: Subject to any disclaimer, the term of this patent is extended or adjusted under 35 U.S.C. 154(b) by 120 days.

(21) Appl. No.: 15/870,404

(22) Filed: Jan. 12, 2018

Related U.S. Application Data

(60) Provisional application No. 62/451,877, filed on Jan. 30, 2017.

(51) Int. Cl.
| | |
|---|---|
| *A44C 17/00* | (2006.01) |
| *G01N 21/87* | (2006.01) |
| *G06F 3/048* | (2013.01) |

(52) U.S. Cl.
CPC .......... *A44C 17/001* (2013.01); *G01N 21/87* (2013.01); *G06F 3/048* (2013.01)

(58) Field of Classification Search
None
See application file for complete search history.

(56) References Cited

U.S. PATENT DOCUMENTS

| | | | | |
|---|---|---|---|---|
| 2006/0164623 A1* | 7/2006 | Wagner | ................... | G01N 21/87 356/30 |
| 2006/0244946 A1* | 11/2006 | Underwood | ........... | G01N 21/87 356/30 |
| 2009/0234754 A1* | 9/2009 | Lapa | ................... | G06Q 30/0278 705/26.1 |
| 2011/0145335 A1* | 6/2011 | Muthyala | ........... | G06Q 30/0603 709/206 |
| 2012/0331422 A1* | 12/2012 | High | ..................... | G06Q 50/00 715/849 |

\* cited by examiner

*Primary Examiner* — Leon Viet Q Nguyen
(74) *Attorney, Agent, or Firm* — Byrne Poh LLP

(57) ABSTRACT

Methods, systems, and media for rating and analyzing diamonds are provided. In some embodiments, the method comprises: receiving, from a user device, a selection of a diamond from a plurality of diamonds; in response to receiving the selection of the diamond, receiving at least one image of the diamond and a plurality of ratings corresponding to the diamond; calculating an eye-cleanliness score corresponding to the diamond that indicates a clarity of the diamond when viewed without magnification and a brilliance score corresponding to the diamond that indicates an amount of light reflected through the diamond based on the at least one image of the diamond and at least one rating of the plurality of ratings corresponding to the diamond; and causing a user interface to be presented on the user device indicates the eye-cleanliness score and the brilliance score.

18 Claims, 6 Drawing Sheets

470

ANALYZE DIAMOND

Enter URL: www.d.com/d143

FIG. 4C

Report 500

Eye-Cleanliness: Good

Brilliance: Fair

Ideal Setting: Platinum

Overall (from 0-5): 4

FIG. 5

METHODS, SYSTEMS, AND MEDIA FOR RATING AND ANALYZING DIAMONDS

CROSS-REFERENCE TO RELATED APPLICATION

This application claims the benefit of U.S. Provisional Patent Application No. 62/451,877, filed Jan. 30, 2017, which is hereby incorporated by reference herein in its entirety.

TECHNICAL FIELD

The disclosed subject matter relates to methods, systems, and media for rating and analyzing diamonds.

BACKGROUND

People may want to purchase a diamond through a website, for example, through an online retailer. Although information about the quality of the diamond or various characteristics of the diamond (e.g., size, cut, color, clarity, etc.) may be available through images, videos, and ratings, it can be difficult to determine an overall impression of the quality of the diamond based on the provided information, and therefore, to determine whether or not to purchase the diamond.

Accordingly, it is desirable to provide new methods, systems, and media for rating and analyzing diamonds.

SUMMARY

Methods, systems, and media for rating and analyzing diamonds are provided.

In accordance with some embodiments of the disclosed subject matter, a method for rating and analyzing diamonds is provided, the method comprising: receiving, from a user device, a selection of a diamond from a plurality of diamonds; in response to receiving the selection of the diamond, receiving at least one image of the diamond and a plurality of ratings corresponding to the diamond; calculating an eye-cleanliness score corresponding to the diamond that indicates a clarity of the diamond when viewed without magnification and a brilliance score corresponding to the diamond that indicates an amount of light reflected through the diamond based on the at least one image of the diamond and at least one rating of the plurality of ratings corresponding to the diamond; and causing a user interface to be presented on the user device indicates the eye-cleanliness score and the brilliance score.

In accordance with some embodiments of the disclosed subject matter, a system for rating and analyzing diamonds is provided, the system comprising: a hardware processor that is programmed to: receive, from a user device, a selection of a diamond from a plurality of diamonds; in response to receiving the selection of the diamond, receive at least one image of the diamond and a plurality of ratings corresponding to the diamond; calculate an eye-cleanliness score corresponding to the diamond that indicates a clarity of the diamond when viewed without magnification and a brilliance score corresponding to the diamond that indicates an amount of light reflected through the diamond based on the at least one image of the diamond and at least one rating of the plurality of ratings corresponding to the diamond; and cause a user interface to be presented on the user device indicates the eye-cleanliness score and the brilliance score.

In accordance with some embodiments of the disclosed subject matter, a non-transitory computer-readable medium containing computer executable instructions that, when executed by a processor, cause the processor to perform a method for rating and analyzing diamonds, the method comprising: receiving, from a user device, a selection of a diamond from a plurality of diamonds; in response to receiving the selection of the diamond, receiving at least one image of the diamond and a plurality of ratings corresponding to the diamond; calculating an eye-cleanliness score corresponding to the diamond that indicates a clarity of the diamond when viewed without magnification and a brilliance score corresponding to the diamond that indicates an amount of light reflected through the diamond based on the at least one image of the diamond and at least one rating of the plurality of ratings corresponding to the diamond; and causing a user interface to be presented on the user device indicates the eye-cleanliness score and the brilliance score.

In accordance with some embodiments of the disclosed subject matter, a system for rating analyzing diamonds is provided, the system comprising: means for receiving, from a user device, a selection of a diamond from a plurality of diamonds; in response to receiving the selection of the diamond, means for receiving at least one image of the diamond and a plurality of ratings corresponding to the diamond; means for calculating an eye-cleanliness score corresponding to the diamond that indicates a clarity of the diamond when viewed without magnification and a brilliance score corresponding to the diamond that indicates an amount of light reflected through the diamond based on the at least one image of the diamond and at least one rating of the plurality of ratings corresponding to the diamond; and means for causing a user interface to be presented on the user device indicates the eye-cleanliness score and the brilliance score.

In some embodiments, the plurality of ratings includes a score indicating a clarity of the diamond.

In some embodiments, the system further comprises means for calculating an overall score corresponding to the diamond based on the eye-cleanliness score and the brilliance score, wherein the user interface indicates the overall score.

In some embodiments, the system further comprises: means for receiving, from the user device, a second selection of a second diamond from the plurality of diamonds; means for calculating a second eye-cleanliness score corresponding to the second diamond and a second brilliance score corresponding to the second diamond; means for calculating a second overall score corresponding to the second diamond based on the second eye-cleanliness score and the second brilliance score; means for ranking the diamond and the second diamond based on the overall score corresponding to the diamond and the second overall score corresponding to the second diamond; and means for causing an indication of the ranking to be presented in the user interface.

In some embodiments, the means for calculating the eye-cleanliness score comprises means for using the at least one image of the diamond and the at least one rating from the plurality of ratings as inputs to a trained machine learning algorithm, wherein the eye-cleanliness score is an output of the trained machine learning algorithm.

In some embodiments, the system further comprises means for determining a setting corresponding to the diamond based on the plurality of ratings corresponding to the diamond, wherein the means for determining the setting comprises means for determining a metal type of the setting, and wherein the user interface indicates the setting.

In some embodiments, the means for determining the setting further comprises means for determining a height of the diamond within the setting.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIGS. 4A-4C show examples of user interfaces for receiving information about diamonds to be analyzed in accordance with some embodiments of the disclosed subject matter.

FIG. 5 shows an example of a user interface for presenting a generated report indicating results of an analysis of a diamond in accordance with some embodiments of the disclosed subject matter.

DETAILED DESCRIPTION

Figure 1:
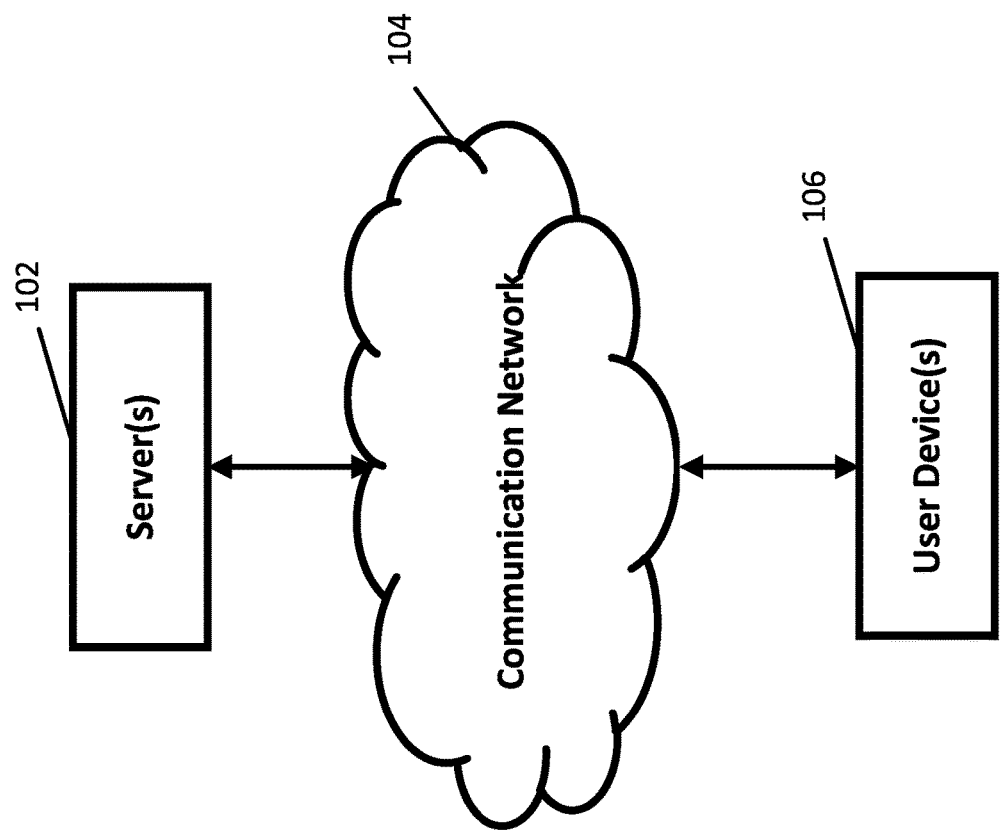
FIG. 1 shows a schematic diagram of an example of a system for analyzing and rating diamonds in accordance with some embodiments of the disclosed subject matter.

In accordance with various embodiments, mechanisms (which can include methods, systems, and media) for rating and analyzing diamonds are provided.

In some embodiments, the mechanisms described herein can analyze images and information relating to a diamond (e.g., images, ratings or scores relating to characteristics such as size, cut, clarity, and color, and/or any other suitable information) and can generate additional ratings and scores that indicate, based on expert opinion, whether the diamond is recommended for purchase. For example, in some embodiments, the additional ratings and scores can indicate an eye-cleanliness of the diamond (e.g., how clear the diamond will look to the human eye when not viewed under magnification), a rating of a quality of the cut of the diamond, a rating of the brilliance of the diamond, an ideal setting for the diamond, and/or any other suitable information. As another example, in some embodiments, the additional ratings and scores can indicate an overall score for the diamond (e.g., that the diamond is recommended, that the diamond is not recommended, that the diamond is "fair," "good," "excellent," and/or any other suitable overall score). In some embodiments, the additional ratings and scores can be included in a report, which can be presented on a user device of a user that requested an analysis of the diamond. In particular, in some embodiments, a user can request an analysis of the diamond via a user interface associated with a particular store or other entity that sells diamonds, as shown in and described below in connection with FIG. 4A.

In some embodiments, the mechanisms described herein can generate ratings, scores, a determination of an ideal setting, and an overall score using any suitable technique or combination of techniques. For example, in some embodiments, the mechanisms can use any suitable artificial intelligence algorithm, as described below in connection with FIG. 3. In some such embodiments, an artificial intelligence algorithm can be trained using a training set of manually annotated diamond instances from any suitable experts. For example, in some embodiments, the training set can include images of diamond instances and associated characteristic ratings (e.g., ratings or scores of size, cut, clarity, color, and/or any other suitable characteristics) and corresponding expert assigned scores for brilliance, cut rating, ideal setting, overall score, and/or any other suitable information. A user-selected diamond can then be analyzed using the trained algorithm, as described below in connection with FIG. 3. In some embodiments, the algorithm can therefore account for interactions between various characteristics (e.g., between a shape of the diamond and a color of the diamond, and/or between any other characteristics) of the diamond in determining an overall rating or score for the diamond. Furthermore, in some embodiments, the algorithm can provide additional information to a user based on available information, for example, by recommending an ideal setting based on available color information or by indicating how clear the diamond will look when viewed without magnification based on images of the diamond.

Turning to FIG. 1, an example 100 of hardware for rating and analyzing diamonds that can be used in accordance with some embodiments of the disclosed subject matter is shown. As illustrated, hardware 100 can include one or more server(s) 102, a communication network 104, and a user device 106.

Server(s) 102 can be any suitable server(s) for receiving information about a diamond (e.g., images of the diamond and scores or ratings indicating size, cut, clarity, color, and/or any other suitable information) and determining a rating for the diamond. For example, in some embodiments, the rating can indicate whether inclusions detected in an image of the diamond are likely to be visible to a human eye without magnification, an ideal setting for the diamond based on the color ratings or image of the diamond, and/or any other suitable ratings as shown in and described below in connection with FIG. 3. As another example, in some embodiments, server(s) 102 can additionally or alternatively determine an overall score for the diamond and/or an overall recommendation for whether to buy the diamond, as shown in and described below in connection with FIG. 3. As yet another example, in some embodiments, server(s) 102 can generate a report that indicates any determined scores or ratings and can transmit the generated report to a user device that requested an analysis of the diamond.

Communication network 104 can be any suitable combination of one or more wired and/or wireless networks in some embodiments. For example, communication network 104 can include any one or more of the Internet, a mobile data network, a satellite network, a local area network, a wide area network, a telephone network, a cable television network, a WiFi network, a WiMax network, and/or any other suitable communication network.

In some embodiments, user device 106 can include one or more computing devices suitable for selecting a diamond for analysis, receiving and displaying a report that indicates an analysis of the selected diamond, and/or performing any other suitable functions. For example, in some embodiments, user device 106 can be implemented as a mobile device, such as a smartphone, mobile phone, a tablet computer, a laptop computer, a vehicle (e.g., a car, a boat, an airplane, or any other suitable vehicle) entertainment system, a portable media player, and/or any other suitable mobile device. As another example, in some embodiments, user devices 106 can be implemented as a non-mobile device such as a desktop computer, a set-top box, a television, a streaming media player, a game console, and/or any other suitable non-mobile device Although only one each of server(s) 102 and user device 106 are shown in FIG. 1 to avoid over-complicating the figure, any suitable one or more of each device can be used in some embodiments.

Figure 2:
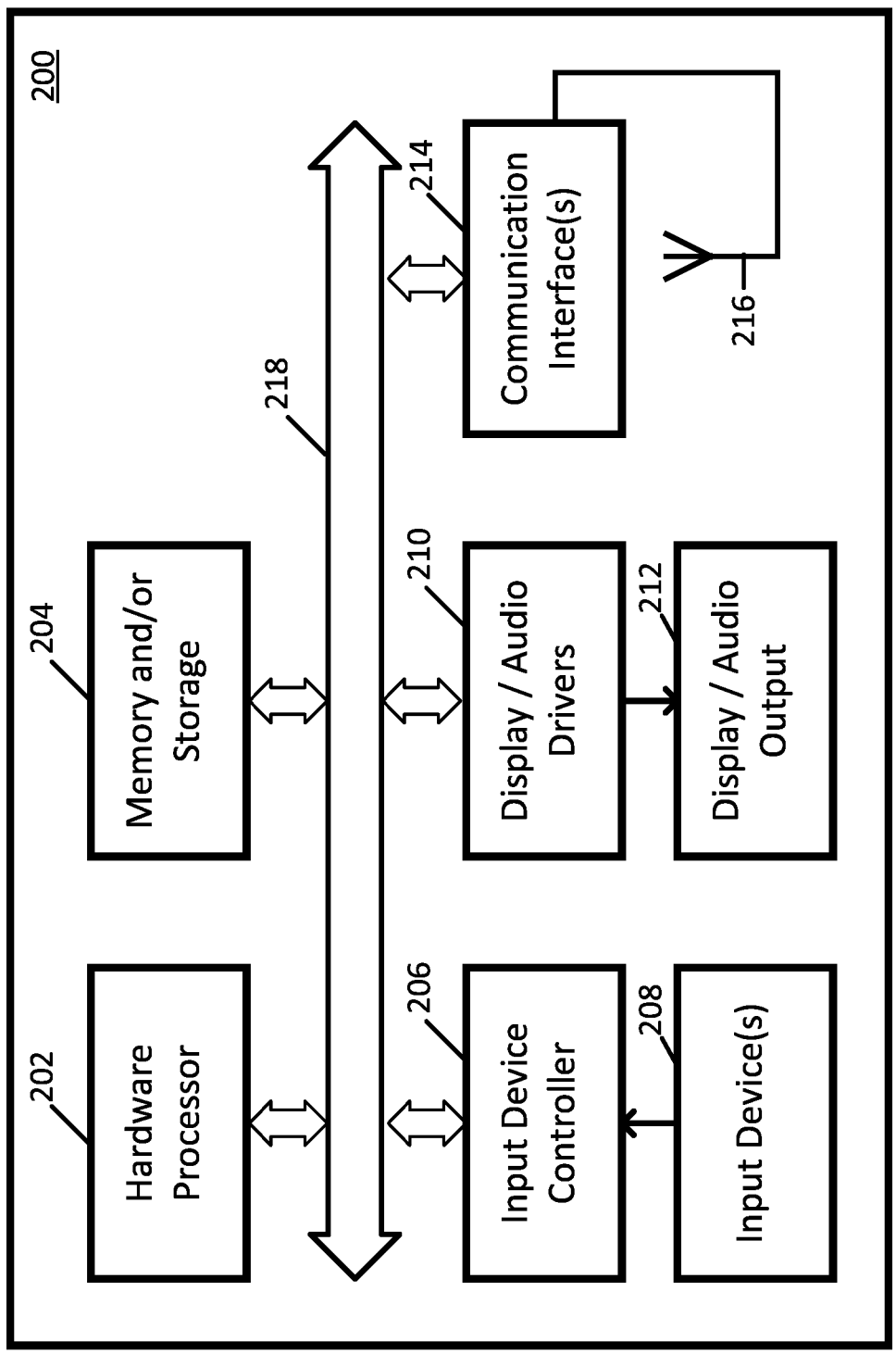
FIG. 2 shows an example of hardware that can be used in a server and/or a user device in accordance with some embodiments of the disclosed subject matter.

Server(s) 102 and/or user device 106 can be implemented using any suitable hardware in some embodiments. For example, in some embodiments, devices 102 and 106 can be implemented using any suitable general purpose computer or special purpose computer. For example, a server may be implemented using a special purpose computer. Any such general purpose computer or special purpose computer can include any suitable hardware. For example, as illustrated in example hardware 200 of FIG. 2, such hardware can include hardware processor 202, memory and/or storage 204, an input device controller 206, an input device 208, display/audio drivers 210, display and audio output circuitry 212, communication interface(s) 214, an antenna 216, and a bus 218.

Hardware processor 202 can include any suitable hardware processor, such as a microprocessor, a micro-controller, digital signal processor(s), dedicated logic, and/or any other suitable circuitry for controlling the functioning of a general purpose computer or a special purpose computer in some embodiments.

Memory and/or storage 204 can be any suitable memory and/or storage for storing programs, data, media content, and/or any other suitable information in some embodiments. For example, memory and/or storage 204 can include random access memory, read-only memory, flash memory, hard disk storage, optical media, and/or any other suitable memory.

Input device controller 206 can be any suitable circuitry for controlling and receiving input from a device in some embodiments. For example, input device controller 206 can be circuitry for receiving input from a touch screen, from one or more buttons, from a voice recognition circuit, from a microphone, from a camera, from an optical sensor, from an accelerometer, from a temperature sensor, from a near field sensor, and/or any other type of input device.

Display/audio drivers 210 can be any suitable circuitry for controlling and driving output to one or more display/audio output circuitries 212 in some embodiments. For example, display/audio drivers 210 can be circuitry for driving an LCD display, a speaker, an LED, or any other type of output device.

Communication interface(s) 214 can be any suitable circuitry for interfacing with one or more communication networks, such as network 104 as shown in FIG. 1. For example, interface(s) 214 can include network interface card circuitry, wireless communication circuitry, and/or any other suitable type of communication network circuitry.

Antenna 216 can be any suitable one or more antennas for wirelessly communicating with a communication network in some embodiments. In some embodiments, antenna 216 can be omitted when not needed.

Bus 218 can be any suitable mechanism for communicating between two or more components 202, 204, 206, 210, and 214 in some embodiments.

Any other suitable components can be included in hardware 200 in accordance with some embodiments.

Figure 3:
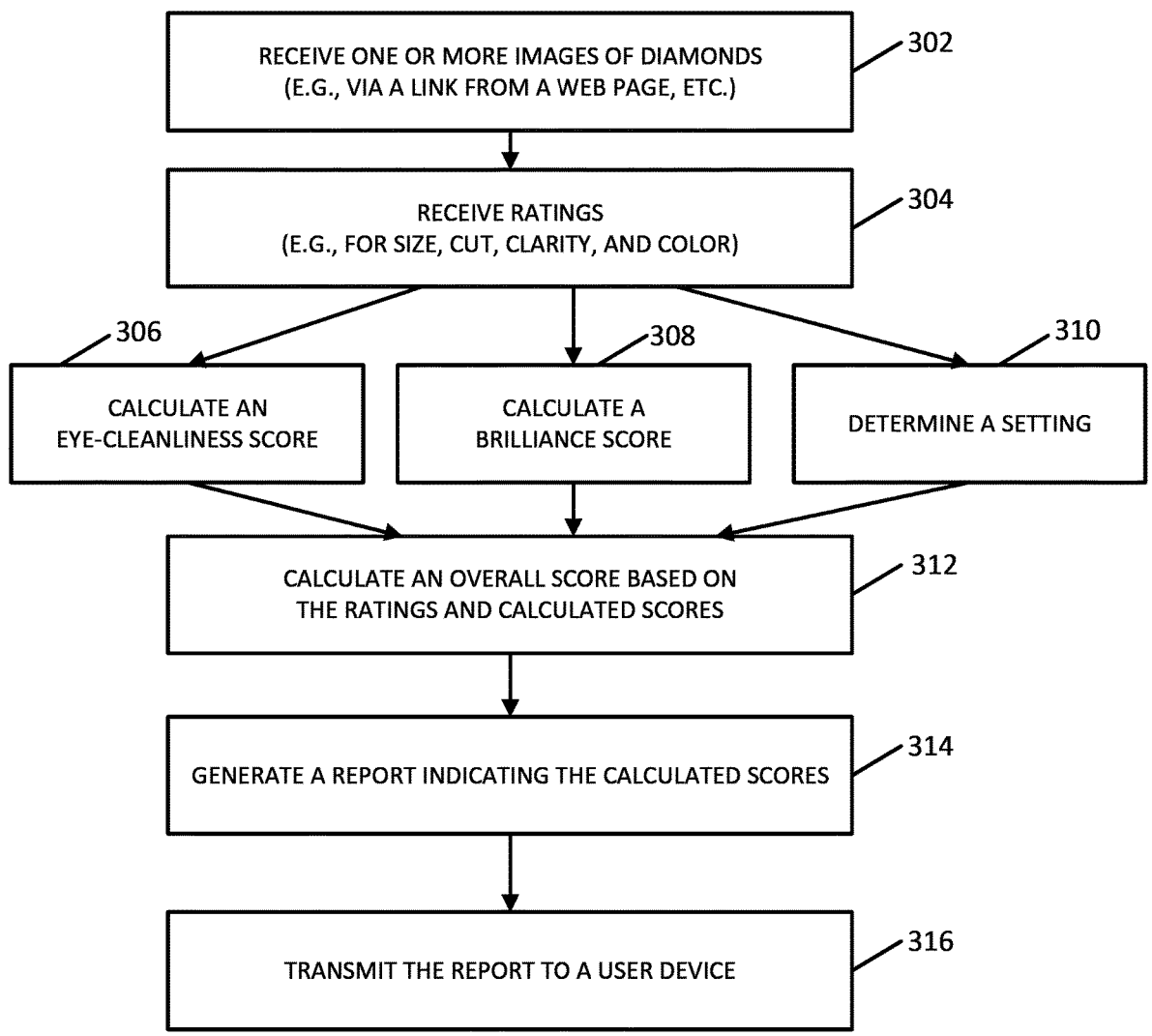
FIG. 3 shows an example of a process for analyzing and rating diamonds in accordance with some embodiments of the disclosed subject matter.

Turning to FIG. 3, an example 300 of a process for analyzing and rating diamonds is shown in accordance with some embodiments of the disclosed subject matter.

Process 300 can begin at 302 by receiving one or more images of a diamond. For example, in some embodiments, the one or more images can be received from a website, such as a website selling diamonds, as shown in and described below in connection with FIG. 4A. In some embodiments, any suitable number (e.g., one, two, five, ten, and/or any other suitable number) of images of the diamond can be received. Additionally, in some embodiments, the images can each be at any suitable magnification level (e.g., no magnification, 10× magnification, and/or any other suitable magnification level). Furthermore, in some embodiments, each of the images can be of the diamond from any suitable perspective (e.g., a top view, a side view, a bottom view, and/or any other suitable view or angle). In some embodiments, the one or more images can be photographs, schematic diagrams that show measurements of various parts of the diamond (e.g., a table of the diamond, facets of the diamond, a girdle of the diamond, and/or any other suitable parts), schematic diagrams that indicate locations of inclusions in the diamond, and/or any other suitable information. Additionally or alternatively, in some embodiments, process 300 can receive one or more videos that show the diamond from any suitable angle, distance or perspective.

Process 300 can receive ratings or scores associated with the diamond at 304. In some embodiments, the ratings or scores can be from any suitable entity (e.g., Gemological Institute of America Inc. of Carlsbad, Calif., and/or any other suitable entity). In some embodiments, the ratings or scores can relate to any suitable characteristics of the diamond, such as size (e.g., in carats, and/or in any other suitable metric), cut, clarity, color, and/or any other suitable characteristics. The received ratings or scores can be in any suitable format(s). For example, a score relating to a size of the diamond can be a numeric value that indicates a size in carats. As another example, a rating or score relating to a clarity of the diamond can be a character or group of characters (e.g., "FL" indicating the diamond is flawless, "VVS1" indicating minor inclusions, "SI1 indicating noticeable inclusions, and/or any other suitable characters) based on any suitable scoring system. As yet another example, a rating or score relating to a color of the diamond can be a character or group of characters (e.g., "D" indicating the diamond is nearly colorless, and/or any other suitable characters) based on any suitable scoring system. As still another example, a rating or score relating to a cut of the diamond can include a ranking score (e.g., "poor," "fair," "very good," a value from 0 to 5, and/or any other suitable ranking value), measurements indicating proportions of various parts of the diamond, and/or any other suitable information.

At blocks 306-310, process 300 can calculate an eye-cleanliness score (indicating how clear the diamond is likely to look to a human eye without magnification), a brilliance score and/or a diamond cut rating, and determine an ideal setting for diamond, respectively. At block 312, process 300 can calculate an overall score for the diamond. In some embodiments, each calculation or determination can be made using any suitable artificial intelligence algorithm(s). For example, in some embodiments, the artificial intelligence algorithm(s) can include supervised machine learning algorithms (e.g., logistic regression, a neural network, a naïve Bayes algorithm, a support vector machine, a decision tree, and/or any other suitable supervised machine learning algorithm), a clustering classification algorithm (e.g., K-nearest neighbors, and/or any other suitable clustering classification algorithm), and/or any other suitable algorithm or combination of algorithms.

In some embodiments, the artificial intelligence algorithm can be trained with any suitable training set. For example, in instances where the artificial intelligence algorithm(s) use supervised machine learning algorithms, the training set can include any suitable number (e.g., 1000, 10,000, 100,000 and/or any other suitable number) of diamond instances (where an instance can include one or more images, any of the scores or ratings received at block 304, and/or any other suitable information) and corresponding manually-tagged scores (e.g., eye-cleanliness scores, brilliance scores, ideal settings, overall scores, and/or any other suitable ratings or scores). As a more particular example, in some embodiments, an artificial intelligence algorithm can be trained to determine an ideal setting using a training set in which a color rating (e.g., "D," indicating a colorless diamond according to any suitable scoring convention) is paired with an expert-identified ideal setting (e.g., platinum, and/or any other suitable material) for any suitable number of training instances.

In instances where a classification algorithm is used to cluster diamond instances into different classifications (e.g., an overall score of "good," an overall score of "poor," a brilliance score of "excellent," and/or any other suitable classification), manual tagging of instances can be used to label classifications assigned by the algorithm.

Note that, in some embodiments, any combination or subset of the images and size, cut, clarity, and color ratings can be used as training data. Additionally, in some embodiments, the image(s) and ratings can be analyzed in any suitable manner to select a subset of the data to use as features or input values for training the artificial intelligence algorithm. For example, in some embodiments, the image(s) and ratings can be analyzed using Principal Components Analysis (PCA) and/or any other suitable technique to select a subset of information to use as features. More detailed techniques for determining an eye-cleanliness score, a brilliance score, and determining a setting are described below.

At block 306, process 300 can determine an eye-cleanliness score for the diamond that indicates how clear the diamond will look to a viewer without magnification. In some embodiments, the eye-cleanliness score can be in any suitable format. For example, in some embodiments, the eye-cleanliness score can be a continuous numeric value (e.g., a decimal value from 0 to 100, and/or along any other suitable scale). As another example, in some embodiments, the eye-cleanliness score can be a categorical value (e.g., "poor," "good," "very good," "excellent," an integer value from 0-5, and/or any other suitable value). In some embodiments, process 300 can determine the eye-cleanliness based on one or more images of the diamond and/or a clarity score associated with the diamond. For example, in some embodiments, the eye-cleanliness score can be determined based on the output of an artificial intelligence algorithm (as described above), which can take as an input the one or more images of the diamond and/or the clarity score associated with the diamond. Note that, in instances where multiple images of the diamond are used as an input to the algorithm, each image can be from a different perspective or angle, thereby showing inclusions at different locations. Additionally or alternatively, in some embodiments, a schematic diagram with markings showing locations of inclusions can be used. Furthermore, in some embodiments, the one or more images can be at different magnification levels (e.g., no magnification, 10× magnification, and/or any other suitable magnification level).

At block 308, process 300 can determine a brilliance score for the diamond that indicates, for example, an amount of light reflected through a top portion of the diamond. In some embodiments, the brilliance score can be in any suitable format. For example, similarly to the eye-cleanliness score, the brilliance score can be a continuous numeric value, a categorical value, and/or any other suitable type of value. In some embodiments, process 300 can determine the brilliance score based on the one or more images of the diamond received at block 302 and/or a cut rating score for the diamond received at block 304. For example, in some embodiments, the brilliance score can be determined based on the output of an artificial intelligence algorithm (as described above), which can take as an input one or more images of the diamond. Note that, in some embodiments, any suitable number (e.g., one, two, five, and/or any other suitable number) of images can be used as inputs to the algorithm, and each of the images can show the diamond from any suitable position or perspective. Additionally, in instances where a rating of a quality of the cut of the diamond is available, the rating can additionally be used as an input. Furthermore, in some embodiments, measurements of various parts of the diamond can additionally or alternatively be used as input values. For example, in some embodiments, measurements indicating a size of the table of the diamond and/or a depth of the diamond can be used as input values.

In some embodiments, process 300 can calculate a cut rating of a quality of a cut of the diamond. For example, in instances where a cut rating is not provided by any entity (e.g., in instances where the diamond is not a round shape, and/or in any other suitable instances), process 300 can determine the cut rating. In some embodiments, the cut rating can be in any suitable format, such as a continuous numeric value, a categorical value, and/or any other suitable type of value. Similarly to the eye-cleanliness score described at block 306 and the brilliance score described above, the cut rating can be determined using an artificial intelligence algorithm as described above.

At block 310, process 300 can determine a setting for the diamond. For example, in some embodiments, process 300 can indicate a metal or a metal alloy (e.g., platinum, white gold, yellow gold, rose gold, and/or any other suitable metal or metal alloy) that is best suited as a setting material for the diamond based on, for example, a color of the diamond. In some embodiments, process 300 can determine the setting using an artificial intelligence algorithm as described above. In some embodiments, the identified settings can additionally include any other suitable information, such as a height setting, a number of prongs of the setting, and/or any other suitable information. In some embodiments, process 300 can use a color rating received at block 304 and/or one or more images of the diamond received at block 302 as inputs to the artificial intelligence algorithm to determine the setting.

Note that, in some embodiments, each of the artificial intelligence algorithms described above in connection with blocks 306, 308, and 310 can be a different type of algorithms. For example, in some embodiments, a particular type of algorithm (e.g., a logistic regression, a neural network, a decision tree, a clustering algorithm, and/or any other suitable type of algorithm) can be selected based on the type of information (e.g., images, scalar values, categorical values, and/or any other suitable type of information) used as inputs for each algorithm and based on a type of information of the output of the algorithm (e.g., a category from a binary classification, a category selected from multiple classes, a continuous numeric value, and/or any other suitable type of output).

Note that, in some embodiments, process 300 can determine any other suitable ratings or scores. For example, in some embodiments, process 300 can calculate a dispersion score that indicates, for example, an amount of light reflected from a crown portion of the diamond. As another example, in some embodiments, process 300 can determine whether a fluorescence score associated with the diamond is a good match to a color score associated with the diamond. For example, in instances where the color score associated with the diamond indicates that the diamond is colorless or nearly colorless, process 300 can determine that the fluorescence score is a good match to the color score if the fluorescence score indicates relatively less fluorescence. As another example, in instances where the color score associated with the diamond indicates that diamond has a noticeable color tint, process 300 can determine that the fluorescence score is a good match to the color score if the fluorescence score indicates relatively more fluorescence. In some embodiments, process 300 can indicate a degree of match in any suitable manner or format, for example, via a value from 0 to 1, where 0 indicates a poor match and 1 indicates a good match, and/or in any other suitable manner.

At 312, process 300 can calculate an overall score for the diamond based on one or more of the image(s) received at block 302, the ratings or scores received at block 304, and/or the scores and settings determined in blocks 306-310. In some embodiments, the overall score can indicate any suitable information and can be in any suitable format. For example, in some embodiments, the overall score can be a binary classification indicating a recommendation of whether or not to buy the diamond. As another example, in some embodiments, the overall score can be a classification of a quality of the diamond (e.g., "good," "poor," "excellent," a score from 0-5, and/or any other suitable classification value).

In some embodiments, process 300 can calculate the overall score in any suitable manner. For example, in some embodiments, any suitable information (e.g., the image(s) received at block 302, ratings or scores received at block 304, scores and settings determined at blocks 306-310, and/or any other suitable information) can be used as inputs to an artificial intelligence algorithm (as described above), which can output the overall score. As another example, in some embodiments, the ratings or scores received at block 304 and/or the scores determined at blocks 306 and 308 can be combined (e.g., using a weighted average, and/or any other suitable type of combination) to calculate the overall score. In some such embodiments, the weight associated with each rating or score used to calculate the weighted average can be modified at any suitable time and based on any suitable information. For example, in some embodiments, the weight for a rating or score can be adjusted based on a manual confirmation of the calculated overall score. As a more particular example, in instances where a weighted average generates a particular overall score (e.g., a 4 on a scale from 0 to 5), and an overall score for the same diamond assigned by an expert is a 2 on a scale from 0 to 5, the weights for the ratings and scores used in the weighted average can be adjusted such that a re-calculation of the overall score is 2 or close to 2. Note that, in some embodiments, a price of the diamond or jewelry can be incorporated into the overall score and/or can modify an overall score. For example, in some embodiments, a higher price can cause the overall score to be modified to be lower than an originally calculated overall score.

Note that, in some embodiments, process 300 can store the overall score and any scores or settings determined at blocks 306-310, for example, in memory 204 of server(s) 102. In some such embodiments, stored ratings or scores can be reused in the future, for example, in response to a second request for an analysis of the diamond (e.g., from a second user).

Process 300 can generate a report indicating the scores and settings determined in blocks 306-310 and the overall score calculated at block 312. For example, in some embodiments, the report can indicate that an eye-cleanliness of the diamond is "good," a brilliance of the diamond is "excellent," that an ideal setting for the diamond is platinum, and that an overall score for the diamond is a 4 on a scale from 0 to 5. As another example, in some embodiments, the report can indicate that experts recommend buying the diamond based on information associated with the diamond. In some embodiments, the report can be in any suitable format and can include any suitable other information, such as links to information relating to various diamond characteristics (e.g., links to information about diamond cut, clarity, and/or color scoring, and/or any other suitable information), links to alternative diamonds that are priced similarly but have received higher scores, and/or any other suitable information.

Process 300 can transmit the report to a user device at 316. For example, as shown in user interface 500 of FIG. 5, the report can be presented as a written report on the user device. In some embodiments, the user device can be one from which a user selected a particular diamond for analysis (e.g., via a user interface associated with a seller of the diamond, and/or in any other suitable manner). Additionally or alternatively, in some embodiments, the report can be presented audibly on the user device. For example, in some embodiments, the user device can present spoken words that indicate content of the received report.

Note that, in some embodiments, process 300 can determine a ranking of multiple diamonds based on scores and ratings generated for each of the diamonds. For example, in some embodiments, process 300 can receive indications of multiple diamonds and corresponding images and scores/ratings for each of the diamonds at blocks 302 and 304, and can calculate additional scores and ratings at blocks 306-312 as described above. Process 300 can then rank each of the diamonds based on, for example, the overall score. In some such embodiments, the report generated at block 314 can indicate the top-ranked diamond from the group of multiple diamonds. Additionally or alternatively, in instances where process 300 is used to rank a group of multiple diamonds and/or select one diamond from the group of multiple diamonds, process 300 can use any suitable artificial intelligence algorithms suitable for ranking (e.g., an ordered logistic regression, and/or any other suitable type of technique(s)). Furthermore, in some such embodiments, training sets used for training an artificial intelligence algorithm can be training sets suitable for ranking multiple choices. For example, in some embodiments, a training set can include information indicating an expert choosing one diamond from two example instances (e.g., based on images, scores or ratings, and/or any other suitable information).

Figure 4A:
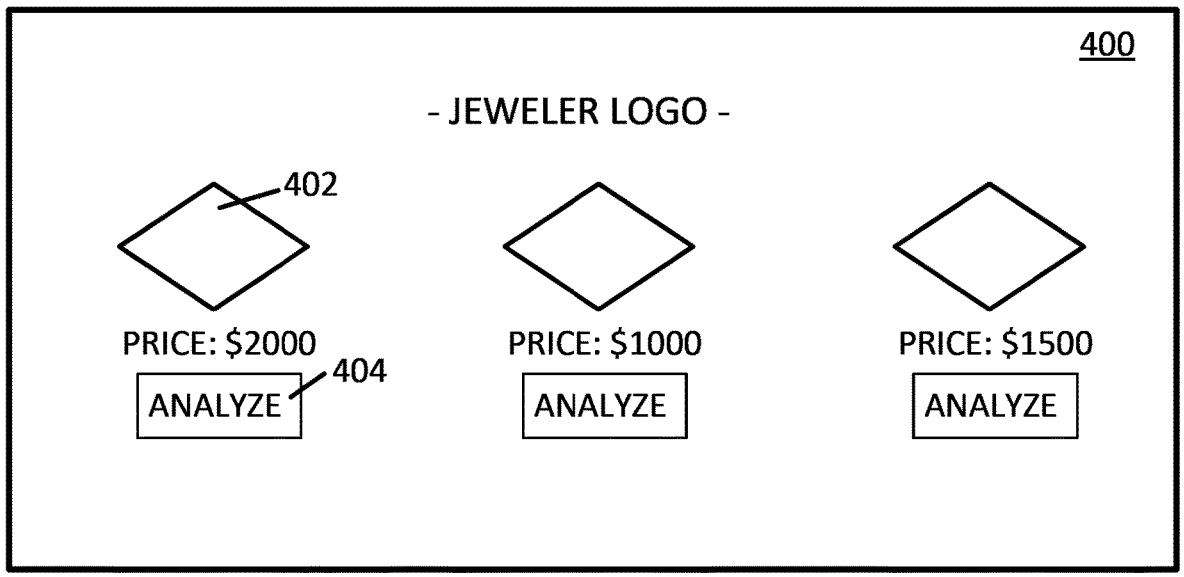
Figure 4B:
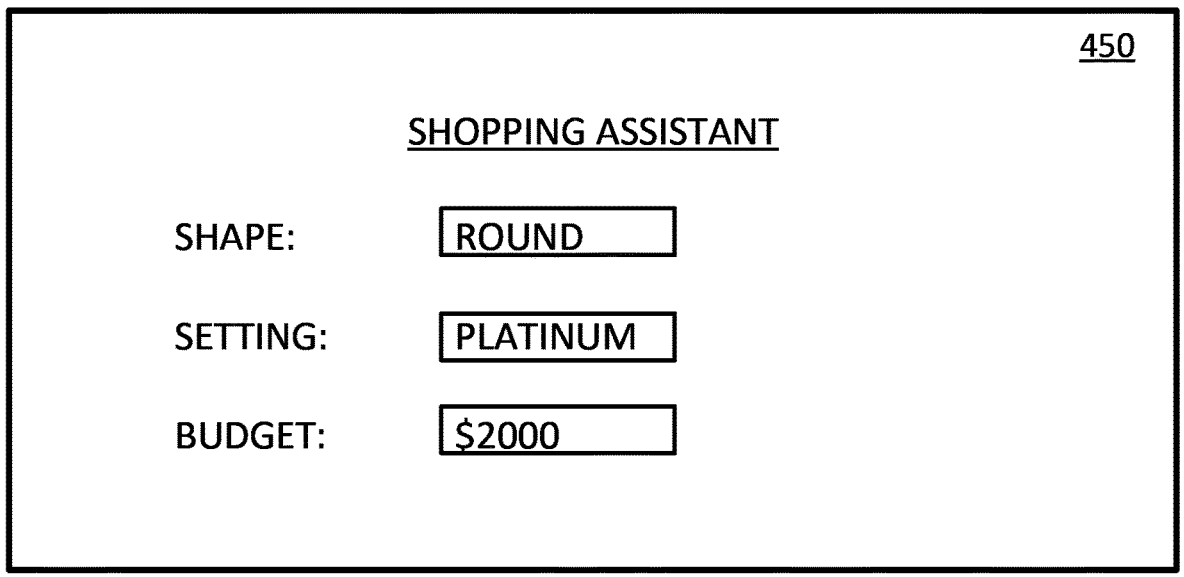

Turning to FIGS. 4A and 4B, examples of user interfaces 400 and 450 for requesting an analysis of diamonds are shown in accordance with some embodiments of the disclosed subject matter. In some embodiments, user interfaces 400 and 450 can be presented on a user device, for example, of a user shopping online for a diamond on a website associated with a particular store or other entity.

User interface 400 shows an example of a user interface in which a user can request an analysis of a particular diamond, such as diamond 402. In some embodiments, user interface 400 can be associated with a particular store that offers multiple diamonds for sale, including diamond 402. In some embodiments, the user can select an analysis input 404, selection of which can cause an identifier of diamond 402 and any other suitable information to be transmitted to server(s) 102 to initiate process 300, as described above. In some such embodiments, after selection of analysis input 404, user interface 500 can be presented on the user device indicating the results of the analysis, as described above in connection with FIGS. 3 and 5.

In some embodiments, process 300 can be used to recommend a particular diamond to a user based on user-specified criteria, as shown in user interface 450. For example, in some embodiments, user interface 450 can receive information that indicates a preferred shape of the diamond (e.g., round, princess, emerald, and/or any other suitable shape), a preferred setting (e.g., platinum, white gold, yellow gold, and/or any other suitable type of setting), and a budget (e.g., a maximum prices the user is willing to pay), and the received information can be transmitted to server(s) 102. Process 300 can then, for example, identify one or more diamonds that meet the user-specified criteria that have been determined to have ratings or scores that exceed a predetermined threshold (e.g., greater than 4 on a scale from 0-5, better than "fair," and/or any other suitable threshold). For example, in some embodiments, process 300 can identify one or more diamonds based on the overall score calculated at block 312, any of the ratings or scores determined at blocks 306-310, and/or any suitable combination, and can recommend the one or more diamonds to the user.

In some embodiments, process 300 can receive an identifier of a diamond by receiving a link (e.g., a Uniform Resource Locator, or URL) to the diamond. For example, in some embodiments, the received link can be a link to an image of the diamond or a link to a page on a website (e.g., a website of a store selling the diamond) that has images of the diamond and/or any other suitable information about the diamond. FIG. 4C shows an example 470 of a user interface for receiving a link to a information about a diamond and/or an image of a diamond. In some embodiments, user interface 470 can be presented on a user device, and a link received via user interface 470 can be transmitted to server(s) 102 to initiate process 300.

It should be understood that at least some of the above described blocks of the process of FIG. 3 can be executed or performed in any order or sequence not limited to the order and sequence shown in and described in the figure. Also, some of the above blocks of the process of FIG. 3 can be executed or performed substantially simultaneously where appropriate or in parallel to reduce latency and processing times. Additionally or alternatively, some of the above described blocks of the process of FIG. 3 can be omitted.

In some embodiments, any suitable computer readable media can be used for storing instructions for performing the functions and/or processes herein. For example, in some embodiments, computer readable media can be transitory or non-transitory. For example, non-transitory computer readable media can include media such as non-transitory magnetic media (such as hard disks, floppy disks, and/or any other suitable magnetic media), non-transitory optical media (such as compact discs, digital video discs, Blu-ray discs, and/or any other suitable optical media), non-transitory semiconductor media (such as flash memory, electrically programmable read-only memory (EPROM), electrically erasable programmable read-only memory (EEPROM), and/or any other suitable semiconductor media), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Accordingly, methods, systems, and media for rating and analyzing diamonds are provided.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A method for rating and analyzing diamonds, comprising:
   receiving, from a user device, a selection of a diamond from a plurality of diamonds;
   in response to receiving the selection of the diamond, receiving at least one image of the diamond and a plurality of ratings corresponding to the diamond;
   calculating an eye-cleanliness score corresponding to the diamond that indicates a clarity of the diamond when viewed without magnification and a brilliance score corresponding to the diamond that indicates an amount of light reflected through the diamond based on the at least one image of the diamond and at least one rating of the plurality of ratings corresponding to the diamond; and
   causing a user interface to be presented on the user device indicates the eye-cleanliness score and the brilliance score,
   wherein calculating the eye-cleanliness score comprises using the at least one image of the diamond and the at least one rating from the plurality of ratings as inputs to a trained machine learning algorithm, and wherein the eye-cleanliness score is an output of the trained machine learning algorithm.

2. The method of claim 1, wherein the plurality of ratings includes a score indicating a clarity of the diamond.

3. The method of claim 1, further comprising calculating an overall score corresponding to the diamond based on the eye-cleanliness score and the brilliance score, wherein the user interface indicates the overall score.

4. The method of claim 3, further comprising:
   receiving, from the user device, a second selection of a second diamond from the plurality of diamonds;
   calculating a second eye-cleanliness score corresponding to the second diamond and a second brilliance score corresponding to the second diamond;
   calculating a second overall score corresponding to the second diamond based on the second eye-cleanliness score and the second brilliance score;
   ranking the diamond and the second diamond based on the overall score corresponding to the diamond and the second overall score corresponding to the second diamond; and
   causing an indication of the ranking to be presented in the user interface.

5. The method of claim 1, further comprising determining a setting corresponding to the diamond based on the plurality of ratings corresponding to the diamond, wherein determining the setting comprises determining a metal type of the setting, and wherein the user interface indicates the setting.

6. The method of claim 5, wherein determining the setting further comprises determining a height of the diamond within the setting.

7. A system for rating and analyzing diamonds, the system comprising:
a hardware processor that is programmed to:
receive, from a user device, a selection of a diamond from a plurality of diamonds;
in response to receiving the selection of the diamond, receive at least one image of the diamond and a plurality of ratings corresponding to the diamond;
calculate an eye-cleanliness score corresponding to the diamond that indicates a clarity of the diamond when viewed without magnification and a brilliance score corresponding to the diamond that indicates an amount of light reflected through the diamond based on the at least one image of the diamond and at least one rating of the plurality of ratings corresponding to the diamond; and
cause a user interface to be presented on the user device indicates the eye-cleanliness score and the brilliance score,
wherein calculating the eye-cleanliness score comprises using the at least one image of the diamond and the at least one rating from the plurality of ratings as inputs to a trained machine learning algorithm, and wherein the eye-cleanliness score is an output of the trained machine learning algorithm.

8. The system of claim 7, wherein the plurality of ratings includes a score indicating a clarity of the diamond.

9. The system of claim 7, wherein the hardware processor is further programmed to calculate an overall score corresponding to the diamond based on the eye-cleanliness score and the brilliance score, wherein the user interface indicates the overall score.

10. The system of claim 9, wherein the hardware processor is further programmed to:
receive, from the user device, a second selection of a second diamond from the plurality of diamonds;
calculate a second eye-cleanliness score corresponding to the second diamond and a second brilliance score corresponding to the second diamond;
calculate a second overall score corresponding to the second diamond based on the second eye-cleanliness score and the second brilliance score;
rank the diamond and the second diamond based on the overall score corresponding to the diamond and the second overall score corresponding to the second diamond; and
cause an indication of the ranking to be presented in the user interface.

11. The system of claim 7, wherein the hardware processor is further programmed to determine a setting corresponding to the diamond based on the plurality of ratings corresponding to the diamond, wherein determining the setting comprises determining a metal type of the setting, and wherein the user interface indicates the setting.

12. The system of claim 11, wherein determining the setting further comprises determining a height of the diamond within the setting.

13. A non-transitory computer-readable medium containing computer executable instructions that, when executed by a processor, cause the processor to perform a method for rating and analyzing diamonds, the method comprising:
receiving, from a user device, a selection of a diamond from a plurality of diamonds;
in response to receiving the selection of the diamond, receiving at least one image of the diamond and a plurality of ratings corresponding to the diamond;
calculating an eye-cleanliness score corresponding to the diamond that indicates a clarity of the diamond when viewed without magnification and a brilliance score corresponding to the diamond that indicates an amount of light reflected through the diamond based on the at least one image of the diamond and at least one rating of the plurality of ratings corresponding to the diamond; and
causing a user interface to be presented on the user device indicates the eye-cleanliness score and the brilliance score,
wherein calculating the eye-cleanliness score comprises using the at least one image of the diamond and the at least one rating from the plurality of ratings as inputs to a trained machine learning algorithm, and wherein the eye-cleanliness score is an output of the trained machine learning algorithm.

14. The non-transitory computer-readable medium of claim 13, wherein the plurality of ratings includes a score indicating a clarity of the diamond.

15. The non-transitory computer-readable medium of claim 13, wherein the method further comprises calculating an overall score corresponding to the diamond based on the eye-cleanliness score and the brilliance score, wherein the user interface indicates the overall score.

16. The non-transitory computer-readable medium of claim 15, wherein the method further comprises:
receiving, from the user device, a second selection of a second diamond from the plurality of diamonds;
calculating a second eye-cleanliness score corresponding to the second diamond and a second brilliance score corresponding to the second diamond;
calculating a second overall score corresponding to the second diamond based on the second eye-cleanliness score and the second brilliance score;
ranking the diamond and the second diamond based on the overall score corresponding to the diamond and the second overall score corresponding to the second diamond; and
causing an indication of the ranking to be presented in the user interface.

17. The non-transitory computer-readable medium of claim 13, wherein the method further comprises determining a setting corresponding to the diamond based on the plurality of ratings corresponding to the diamond, wherein determining the setting comprises determining a metal type of the setting, and wherein the user interface indicates the setting.

18. The non-transitory computer-readable medium of claim 17, wherein determining the setting further comprises determining a height of the diamond within the setting.

* * * * *